(12) United States Patent
Ovsianikov et al.

(10) Patent No.: US 11,931,954 B2
(45) Date of Patent: Mar. 19, 2024

(54) METHOD OF PRODUCING A TEST BODY FOR DIFFUSION TENSOR IMAGING

(71) Applicants: Technische Universität Wien, Vienna (AT); Medizinische Universität Wien, Vienna (AT)

(72) Inventors: Aleksandr Ovsianikov, Vienna (AT); Peter Gruber, Vienna (AT); Christian Windischberger, Vienna (AT); Zoltan Nagy, Zurich (CH)

(73) Assignee: TECHNISCHE UNIVERSITAT WIEN, Vienna (AT)

( * ) Notice: Subject to any disclaimer, the term of this patent is extended or adjusted under 35 U.S.C. 154(b) by 486 days.

(21) Appl. No.: 17/415,416

(22) PCT Filed: Dec. 20, 2019

(86) PCT No.: PCT/AT2019/000035
§ 371 (c)(1),
(2) Date: Jun. 17, 2021

(87) PCT Pub. No.: WO2020/124106
PCT Pub. Date: Jun. 25, 2020

(65) Prior Publication Data
US 2022/0111581 A1   Apr. 14, 2022

(30) Foreign Application Priority Data
Dec. 20, 2018   (EP) .................... 18000986

(51) Int. Cl.
*B29C 64/129*   (2017.01)
*B33Y 10/00*   (2015.01)
(Continued)

(52) U.S. Cl.
CPC ............ *B29C 64/129* (2017.08); *B33Y 10/00* (2014.12); *B33Y 70/00* (2014.12);
(Continued)

(58) Field of Classification Search
None
See application file for complete search history.

(56) References Cited

U.S. PATENT DOCUMENTS

| 9,880,251 B2* | 1/2018 | Kerins | G01R 33/4806 |
| 2006/0195030 A1* | 8/2006 | Ogrezeanu | A61B 5/055 |
| | | | 600/419 |

(Continued)

FOREIGN PATENT DOCUMENTS

WO   2017/017163 A1   2/2017

OTHER PUBLICATIONS

International Search Report dated Apr. 29, 2020, issued in corresponding International Application No. PCT/AT2019/000035 with English translation (6 pgs.).

(Continued)

*Primary Examiner* — Yung-Sheng M Tsui
(74) *Attorney, Agent, or Firm* — Pillsbury Winthrop Shaw Pittman LLP

(57) ABSTRACT

A method of producing a test body for diffusion tensor imaging, which comprises a plurality of channels in a structuring material, the channels preferably having a maximum cross-section of 625 μm², wherein a virtual model of the test body is created and the virtual model is fed to a structuring device which produces the test body by means of a 3D printing-based, in particular lithography-based, structuring process, the structuring process being designed as a multiphoton lithography process, in particular as a multiphoton absorption process, in which the structuring material containing a photosensitizer or photoinitiator is irradiated in a location-selective manner, wherein the radiation is successively focused on focal points lying within the structuring material, resulting in that in each case a volume element of the material located in the focal point is subjected to a (Continued)

change in state by means of a photochemical reaction as a result of multiphoton absorption.

20 Claims, 4 Drawing Sheets

(51) Int. Cl.
| | |
|---|---|
| *B33Y 70/00* | (2020.01) |
| *G01R 33/563* | (2006.01) |
| *G01R 33/58* | (2006.01) |
| *G03F 7/029* | (2006.01) |
| *G03F 7/20* | (2006.01) |
| *B29K 105/00* | (2006.01) |
| *B29L 31/40* | (2006.01) |

(52) U.S. Cl.
CPC ....... *G01R 33/56341* (2013.01); *G01R 33/58* (2013.01); *G03F 7/029* (2013.01); *G03F 7/2053* (2013.01); *B29K 2105/0005* (2013.01); *B29L 2031/40* (2013.01)

(56) References Cited

U.S. PATENT DOCUMENTS

| | | | | |
|---|---|---|---|---|
| 2008/0284437 | A1* | 11/2008 | Yoo | A61B 5/055 |
| | | | | 324/318 |
| 2009/0058417 | A1* | 3/2009 | Yanasak | G01R 33/58 |
| | | | | 324/307 |
| 2011/0043206 | A1* | 2/2011 | Kimura | G01R 33/56341 |
| | | | | 324/309 |
| 2016/0363644 | A1* | 12/2016 | Wang | G01R 33/58 |
| 2017/0184696 | A1* | 6/2017 | Zuccolotto | G01R 33/56341 |
| 2018/0055408 | A1 | 3/2018 | Song et al. | |
| 2018/0257297 | A1 | 9/2018 | Matheu | |
| 2018/0327715 | A1 | 11/2018 | Espinosa-Hoyos et al. | |
| 2018/0335498 | A1* | 11/2018 | Attariwala | A61B 5/055 |
| 2019/0057623 | A1* | 2/2019 | Magsood | B29C 39/003 |
| 2019/0383895 | A1* | 12/2019 | Zuccolotto | G01R 33/56341 |
| 2021/0018584 | A1* | 1/2021 | Golay | G01R 33/5608 |

OTHER PUBLICATIONS

Written Opinion of the International Search Authority dated Apr. 29, 2020, issued in corresponding International Application No. PCT/AT2019/000035 (7 pgs.).

Warren R. Zipfel et al., "Nonlinear magic: multiphoton microscopy in the biosciences", Nature Biotechnology, Nov. 2003, pp. 1369-1377, vol. 21, No. 11.

Daniela Espinosa-Hoyos et al., "Engineered 3D-printed artificial axons", www.nature.com, Scientific Reports, (2018) 8:478, pp. 1-13.

Nirveek Bhattacharjee et al., "The upcoming 3D-printing revolution in microfluidics", The Royal Society of Chemistry, Lab on a Chip, May 21, 2016, pp. 1720-1742, vol. 16, No. 10.

Noga Livnat et al., "Three-dimensional guidance of DRG neurite outgrowth using multi-photon photo-ablation", Proceedings of the 4th International IEEE EMBS Conference on Neural Engineering Antalya, Turkey, Apr. 29-May 2, 2009, pp. 116-119.

* cited by examiner

METHOD OF PRODUCING A TEST BODY FOR DIFFUSION TENSOR IMAGING

CROSS-REFERENCE TO RELATED APPLICATIONS

This application is the U.S. national stage entry of PCT/AT2019/000035, filed Dec. 20, 2019, which claims priority to European Patent Application No. 18000986.2, filed Dec. 20, 2018, the entire contents of both of which are herein incorporated by reference in their entireties.

The invention relates to a method of producing a test body for diffusion tensor imaging which has a plurality of channels in a structuring material. The invention relates in particular to test bodies with which diffusion movements along axon fibers of a nerve tissue, in particular the white matter of a brain, can be simulated.

With the help of a test body of the type mentioned at the beginning, magnetic resonance tomographs (MRT) can be calibrated more efficiently and algorithms can be implemented for better differentiation of the axon courses. The reliable differentiation of the axon courses is of essential importance because an incorrect differentiation between crossing, tangent and passing axons represents a considerable risk, for example when planning operations in neurosurgery.

The invention relates generally to the simulation of any structure with regard to diffusion movements, this also including technical applications outside the human body. The invention particularly relates to the replication of any area of human nervous tissue with respect to diffusion motions. The invention preferably relates to the simulation of diffusion movements in a partial area of the human brain.

Diffusion-weighted magnetic resonance imaging (DW-MRI) is an imaging process that uses magnetic resonance tomography to measure the diffusion movement of water molecules in body tissue and display it in spatial resolution. In diffusion tensor imaging (DTI), the directional dependency of the diffusion is also determined. Within a sample, the microstructure of the material determines the mobility of the water molecules and makes them direction-dependent. This directional dependence provides information about the anisotropy and microstructure of the material.

An interesting application of DTI is to study the white matter in the brain, which contains a network of bundles of parallel axon fibers. In this environment, the orientation-dependent diffusion occurs, since the diffusion along the axon direction is much more pronounced than it is transverse to the fiber direction. This preferred diffusion direction provides information about the orientation of the fibers. However, the reliability and quality of the results obtained from the DTI depend on the recorded data, which can be impaired, for example, by a low signal-to-noise ratio, patient movements during the scan, chemical shift or inhomogeneities of the magnetic field or poor resolution. Furthermore, the spatial resolution of the DTI is several orders of magnitude lower than the dimensions of the fibers, and entangled or crossing fibers may not be properly resolved. In view of these uncertainties, it is desirable to check the accuracy of the results and the measured diffusion parameters and fiber directions quantitatively in order to avoid misinterpretations. This can be achieved by direct measurements on test bodies.

Test bodies for diffusion tensor imaging comprise a large number of channels in a structuring material, the individual channels allowing the diffusion movements along the axon fibers to be simulated. In order to simulate the bundles of parallel axon fibers, a test body must comprise corresponding bundles of parallel channels, whereby these can be implemented as intersecting, tangent and mutually passing-by bundles of channels. In order to be able to operate a successful tractography of diffusion tensor imaging data obtained on a test body, very small channel diameters are essential. Based on the mean diffusion length of water molecules at body temperature of around 25 µm, the maximum channel diameter is around 20 µm. At the same time, the channel walls must also be as thin as possible in order to maximize the total proportion of water molecules and thus the achievable MR signal strength. In addition, the high-resolution measurement of very small samples or test bodies is not possible with conventional magnetic resonance tomographs for human use. The problem is essentially based on the limited strength of the magnetic field gradients required for spatial coding.

The production of test bodies with a closely arranged, open-pore channel system therefore requires a production process which has high-resolution microstructuring properties. The structure of the test body should have both material stability and a clear diffusion difference between the structuring material and the channels. In addition, it should be ensured that sharply delimited channels are produced, since only clearly closed and defined edges at the transition to the channels enable the precise detection of directed diffusion. Finally, the process should be economical and production should therefore be possible with a sufficient throughput.

The present invention aims to provide a manufacturing method for test bodies which meets the above-mentioned requirements.

To solve this problem, the invention provides a method of producing a test body for diffusion tensor imaging, which comprises a plurality of channels in a structuring material, the channels preferably having a maximum cross-section of 625 µm$^2$, wherein a virtual model of the test body is created and the virtual model is fed to a structuring device which produces the test body by means of a 3D printing-based, in particular lithography-based, structuring process, the structuring process being designed as a multiphoton lithography process, in particular as a multiphoton absorption process, in which the structuring material containing a photosensitizer or photoinitiator is irradiated in a location-selective manner, wherein the radiation is successively focused on focal points lying within the structuring material, resulting in that in each case a volume element of the material located in the focal point is subjected to a change in state by means of a photochemical reaction as a result of multiphoton absorption and in that the plurality of channels is created in the structuring material.

The invention is thus based on the finding that multiphoton absorption, in particular two-photon absorption (2PA) with its high-resolution microstructuring properties, is a suitable method for generating test bodies which have the properties required for DTI calibration. With 2PA, permanent, long-term stable and cost-effective structures can be created.

Due to the use of multiphoton absorption (MPA) for the lithography-based production of the test body, components with high resolution can be provided. The method used is based on the fact that the change in state of the material only takes place in that area of the beam path in which there is a photon density sufficient for MPA. The highest photon density occurs at the focal point of the optical imaging system, which is why MPA only changes the state of the material at the focal point. As a result of such an inherent reduction in the active volume, the achievable resolution is much higher than with conventional stereolithography-based methods and can be below 100 nanometers.

Another advantage of multiphoton absorption methods is the possibility of adapting the volume of the focal point to the respective requirements by means of optical devices arranged in the beam path, whereby the volume of the respective volume element of the structuring material subject to the change of state can be adjusted in a simple manner. The adaptability of the volume of the volume elements is particularly advantageous in the formation of channel structures, as they are characteristic of test bodies for diffusion tensor imaging, whereby the procedure can preferably be such that the volume is adapted to the achievable channel cross-section or to the channel spacing between adjacent channels. In particular, this takes place in such a way that the volume element or its cross section corresponds exactly to the channel cross section or a preferably whole-numbered fraction thereof or that the volume element or its extension corresponds exactly to the channel spacing or an integral fraction thereof. The channel cross-section or the material filling the distance between adjacent channels can thus be structured by a single volume element or an integral multiple thereof.

According to a preferred embodiment of the invention, the procedure can be such that the focal point volume, after it has been set for the production of a test body, is left unchanged for the entire production process. Alternatively, the focal point volume can be varied during the method so that the test body comprises volume elements of a first group that have a changed state and volume elements of a second group that have a changed state, the volume elements of the first group having a smaller volume than the volume elements of the second group. The variation of the focal point volume can also be used to form channels with diameter gradients along the channel. This can be a linear change in the diameter along the length of the channel or an abrupt change in the diameter.

The structuring process according to the invention can be designed as an additive or as a subtractive method.

In the case of an additive process, the respective volume element of the material located in the focal point is solidified. A structuring material is thus used that is flowable in its initial state and that is kept in a container during the structuring process, while the individual volume elements are solidified by the effect of the beam directed at the respective focal point, so that the test body is built up successively from the solidified volume elements. The photosensitizer and/or photoinitiator contained in the structuring material is designed to initiate photopolymerization in the structuring material. The exposure is preferably carried out from below through a bottom, transparent to the electromagnetic radiation, of the container receiving the flowable material.

At least one acrylate- or methacrylate-based photopolymer, such as a 1:1 mixture of ethoxylated (20/3) trimethylolpropane triacrylate (ETA) and trimethylolpropane triacrylate (TTA), mixed with a photoinitiator, such as M2CMK, is preferably suitable as the material for structuring by means of the additive multiphoton absorption process. In particular, an amount of 5 μmol M2CMK per gram of the ETA-TTA mixture can be used. M2CMK is a substance with the following molecular structure:

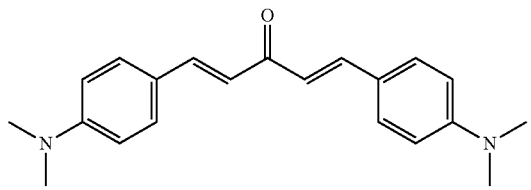

In the course of tests, it has been shown that test bodies made from an ETA-TTA mixture could meet all material requirements. The MR measurements carried out showed clear anisotropy in the diffusion patterns of the water molecules and thus allowed for the first time the successful application of MR-based tractography in 3D-printed objects.

In the case of the subtractive method, the respective volume element of the material located in the focal point is photo-degraded. A structuring material is therefore used that is solid or semi-solid in the initial state, in which the individual channels are formed by photodegradation. To form the channels, the radiation is successively focused on focal points within the material which are located in the respective channel to be formed, as a result of which the volume elements of the material located at the focal points are photo-degraded. After washing out the photosensitizer and at least some of any cleavage products, a channel is created from the totality of connected photodegraded volume elements. The photodegradation can take place here using a photosensitizer or a photoinitiator.

In the context of the invention, the term "photodegradation" is to be understood as any process in which material areas get less cross-linked due to the irradiation, without the material network necessarily being completely degraded. It is only necessary that an area with changed diffusion properties is created, which area is to be understood as a "channel" in the context of the invention.

The two-photon photosensitizer contained in the structuring material must be suitable for bringing about a photochemical cleavage of bonds contained in the structuring material. Materials in which photochemical cleavage of bonds can be brought about by admixing two-photon photosensitizers and using electromagnetic radiation are known from the prior art and can be used in the context of the present invention.

In this context, a particularly advantageous embodiment provides that the two-photon photosensitizer is designed for the photochemical cleavage of photolabile bonds contained in the structuring material, in particular disulfide bonds, wherein the photosensitizer transfers the absorbed energy to the photolabile bonds, in particular disulfide bonds, as a result of two-photon absorption without experiencing intramolecular cleavage, and thereby causes their cleavage.

In a preferred embodiment, the structuring material contains the photolabile bonds, in particular disulfide bonds, to be cleaved in a matrix formed by a polymer network, preferably a polymer network crosslinked via these bonds.

The polymer network is preferably a gel, preferably a hydrogel.

The mixing of the two-photon photosensitizer with the gel is carried out according to further preferred embodiments of the invention in a simple manner by allowing the gel to swell with a solution of the two-photon photosensitizer in a suitable solvent, for example water in the case of hydrogels, in order to distribute the two-photon photosensitizer as evenly as possible in the gel before the irradiation takes place.

Such a solution of the two-photon photosensitizer preferably has a relatively low concentration of only about 0.01 mM to about 1 mM, more preferably of about 0.05 mM to about 0.5 mM, in particular of about 0.1 mM, in order to save costs and to prevent excessive cleavage reactions or, depending on the composition of the gel, any side reactions.

According to the present invention, all known two-photon photosensitizers can in principle be used, but a photosensitizer with a two-photon cross-section σ2P>1 GM (Goeppert-Mayerin) in the relevant spectral range is preferably used, in order not to have to choose an excessively high light intensity and/or long exposure time.

In preferred embodiments, according to the present invention, a two-photon photosensitizer selected from the class of the benzylidene ketones, preferably one of the initiators P2CK, G2CK and E2CK shown below, is used:

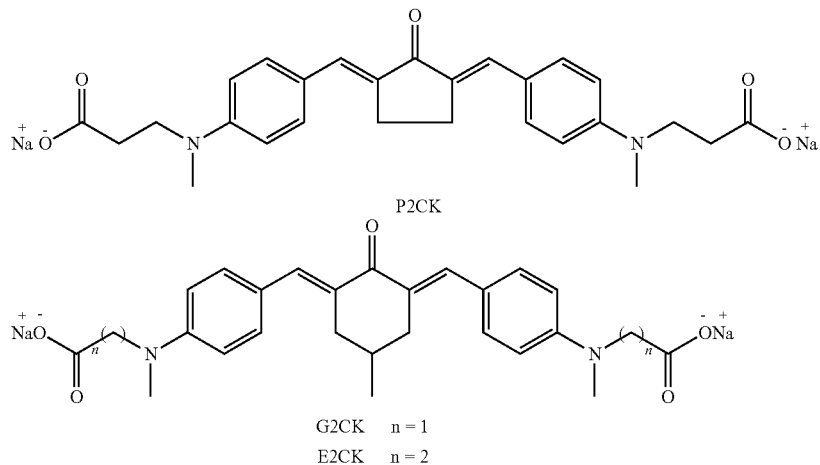

In other preferred embodiments, the benzylidene initiator R1 shown below is used according to the present invention:

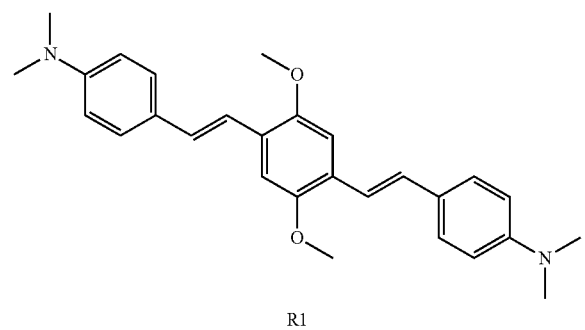

The principle of multiphoton absorption is based on the fact that the photochemical process only takes place in those areas of the beam path in which there is sufficient photon density for multiphoton absorption. The highest photon density occurs in the focal point of the optical imaging system, so that the multiphoton absorption occurs with sufficient probability only in the focal point. Outside the focal point, the photon density is lower, so that the probability of multiphoton absorption outside the focal point is too low to cause an irreversible change in the material through a photochemical reaction. The electromagnetic radiation can pass through the material largely unhindered in the wavelength used and there is an interaction between photosensitive material and electromagnetic radiation only at the focal point. The principle of multiphoton absorption is described, for example, in Zipfel et al, "Nonlinear magic: multiphoton microscopy in the biosciences", NATURE BIOTECHNOLOGY VOLUME 21 NUMBER 11 Nov. 2003.

The source for the electromagnetic radiation can preferably be a collimated laser beam. The laser can emit one or more, fixed or variable wavelengths. In particular, it is a continuous or pulsed laser with pulse lengths in the nanosecond, picosecond or femtosecond range. A pulsed femtosecond laser offers the advantage that a lower average power is required for the multiphoton absorption.

The performance of the electromagnetic radiation and the exposure time influence the quality of the component produced. By adapting the radiation power and/or the exposure time, the volume of the focal point can be varied within a narrow range. If the radiation output is too high, additional processes occur that can damage the component. If the radiation output is too low, no permanent change in material properties can occur. For every photosensitive material there are therefore typical construction process parameters that are associated with good component properties.

As already mentioned, in a preferred embodiment of the invention, the focal point volume can be varied during the method in such a way that the test body comprises state-changed, in particular solidified or photo-degraded, volume elements of a first group and state-changed, in particular solidified or photo-degraded, volume elements of a second group, the volume elements of the first group having a smaller volume than the volume elements of the second group. The mentioned variation of the focal point volume is not based on a change in the intensity of the electromagnetic radiation used. Rather, the (optimal) radiation intensity selected for the manufacturing process is used, which is advantageously left unchanged during the process. The method according to the invention is therefore preferably carried out in such a way that the change in the focal point volume is carried out while the radiation intensity remains the same, the average power of the electromagnetic radiation used being adapted accordingly.

The volume of an exposed point after the treatment step with the typical process parameters is therefore understood as the focal point volume. The change in the focal point volume is understood to mean a change in the spatial intensity distribution in the focal point. The spatial intensity distribution of the focal point can be changed in one or more directions. For example, by reducing the effective numerical aperture of the optical imaging system, the intensity distribution can be increased in all three spatial directions. When using a diffractive optical element, the focus can be changed to a line or area, or the number of focal points can be increased.

By varying the focal point during the production of the test body, the advantage of high resolution is retained with a small focal point volume, while a high writing speed (measured in mm³/h) can be achieved with a large focal point volume.

In an additive manufacturing process, the variation of the focal point volume can be used in such a way that the first group of solidified volume elements form the channel walls and the second group of solidified volume elements form the regions lying between the channel walls. Small focal point volumes are thus used for the sharp delimitation of the channels, whereas large focal point volumes are used to fill the interior spaces lying therebetween and, if necessary, for the edge areas of the test body. The channel walls, which consist of the solidified volume elements of the first group, have at least the thickness of a volume element. The channel walls can also have the thickness of two, three or more volume elements. However, the thickness of the channel walls consisting of the solidified volume elements of the first group is limited in such a way that an area still remains between the channel walls of adjacent channels which is formed from the solidified volume elements of the second group.

In a subtractive manufacturing process, the variation of the focal point volume can be used in such a way that the first group of photo-degraded volume elements form the channel walls and the second group of photo-degraded volume elements form the interior of the channels. Small focal point volumes are thus used for the sharp delimitation of the channels, whereas large focal point volumes are used for photo-degrading the interior space delimited by the walls.

In a preferred procedure, the volume of the focal point is varied during the method in such a way that the state-changed volume elements of the first group have a volume that is less than 50%, preferably less than 10%, of the volume of the state-changed volume elements of the second group.

The focus volume is preferably varied in such a way that the largest focal point volume during manufacture of the test body is greater than 50 µm³, preferably greater than 100 µm³, in particular greater than 10,000 µm³.

The focus volume is preferably varied in such a way that the smallest focal point volume during manufacture of the test body is less than 50 µm³, preferably less than 1 µm³, in particular less than 0.05 µm³.

The cross-section of the channels formed in the test body can be selected according to the respective requirements. The cross section is preferably square, rectangular, circular or oval.

As already mentioned, the cross-sectional area of the channels is less than 625 µm². The cross-sectional area is preferably selected to be less than 100 µm², in particular less than 50 µm².

The channels can here also be formed with a diameter gradient along the channel. This can be a linear change in the diameter along the length of the channel or an abrupt change in the diameter.

In order to be able to simulate the topography of the bundles of parallel axon fibers typically present in a human brain, a preferred embodiment of the invention provides that the test body comprises a first group of channels and a second group of channels, the channels of the first group and the channels of the second group not running parallel to each other. The first group of channels forms a first channel bundle and the second group of channels forms a second channel bundle.

In particular, the channels of the first group cross the channels of the second group, preferably at a right angle.

Furthermore, the first channel bundle and the second channel bundle can be designed to be tangent. In this context, it is preferably provided that the channels of the first and the second group are curved and have a common tangent.

According to a separate aspect of the present invention, the use of a test body produced by the method according to the invention for calibrating a magnetic resonance tomograph is claimed, the test body being subjected to a diffusion-weighted MRT, in particular diffusion tensor imaging and/or multi-shell or q-ball imaging, and the imaging data obtained being subjected to a quantitative analysis and/or a tractography, the result of the quantitative analysis being compared with the diffusion reference values, while the tractography result is compared with the actual course of the channels in the test body and any deviations are used to calibrate the magnetic resonance tomograph. It goes without saying that the channels can be filled with a contrast medium before the test body is subjected to the diffusion-diffusion MRT.

The invention is explained in more detail below with reference to exemplary embodiments schematically shown in the drawing.

Figure 1:
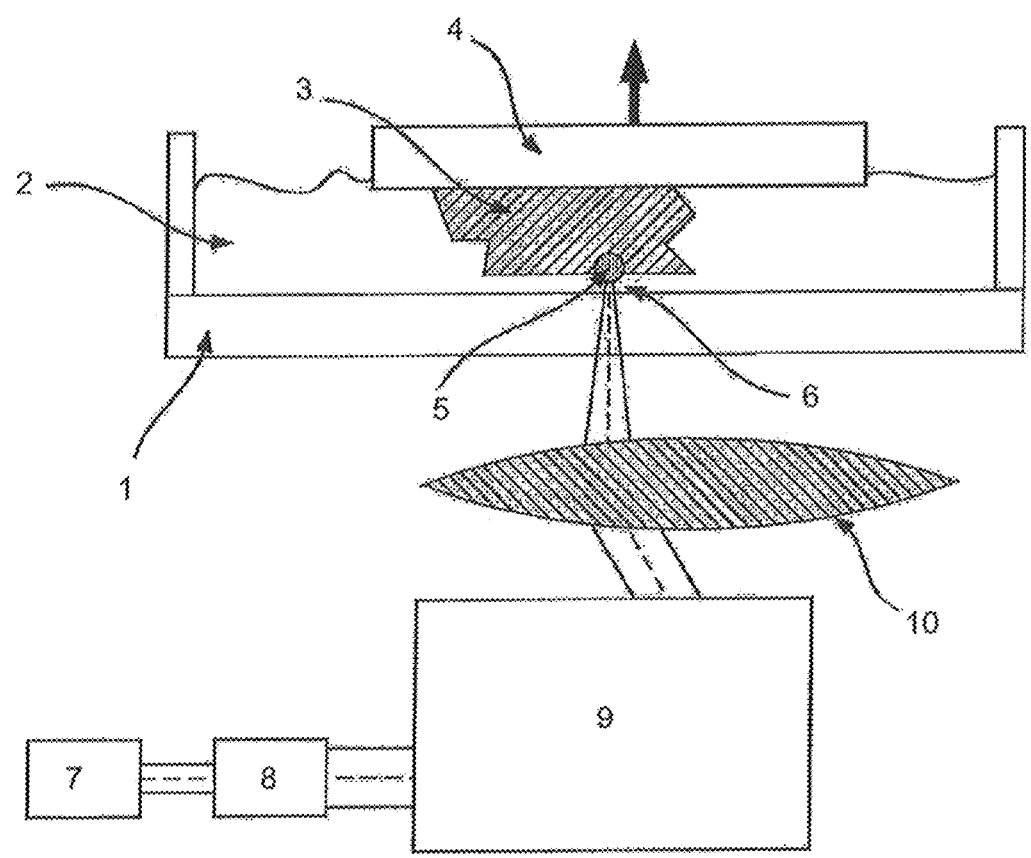
FIG. 1 shows a device for carrying out the method according to the invention.

In FIG. 1 it can be seen that an electromagnetic wave emitted by the laser 7 is guided through a unit for changing the focal point volume 8 and over a beam deflection unit 9 and focused by means of an optical imaging system 10 through a transparent base plate 1 into a photosensitive material 2. At the focal point 5 of the optical imaging system 10, the state of the photosensitive material 2 changes, with which the component 3 is built up. The component 3 is suspended on a construction platform 4, which can be moved in the vertical direction. After the current layer has been completely exposed, the construction platform 4 is raised and the next layer is exposed. By using a laser 7 with a high peak power, the use of multiphoton absorption is possible so that the change in state of the material only takes place in the focus 5, but not in the optically "dead" zone 6 between the tub bottom 1 and the construction platform or the component that has already been formed. This means that the component cannot adhere to the transparent base plate 1.

All elements in FIG. 1 are shown only symbolically and can be developed further as desired and according to the knowledge of the person skilled in the art, for example by using additional lens systems, diaphragms, mirrors, filters or beam splitters.

Figure 2:
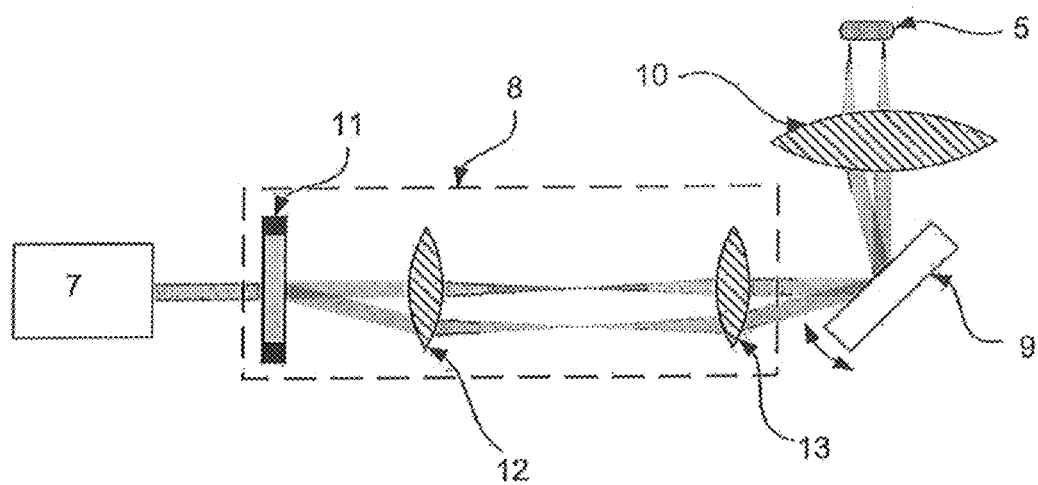
FIG. 2 shows a unit for focus volume adjustment.

FIG. 2 schematically shows the unit 8 for changing the focal point volume. The unit comprises a diffractive optical element 11 which splits the incoming beam into two beams which pass through a system of two lenses 12 and 13. The beam is split with the aim of creating two points next to each other in the focal plane. If both points overlap, one can also speak of a line. Alternatively, the element 11 can be designed as a rapidly moving beam deflection system with which the width of the focus volume can be adjusted.

Figure 3:
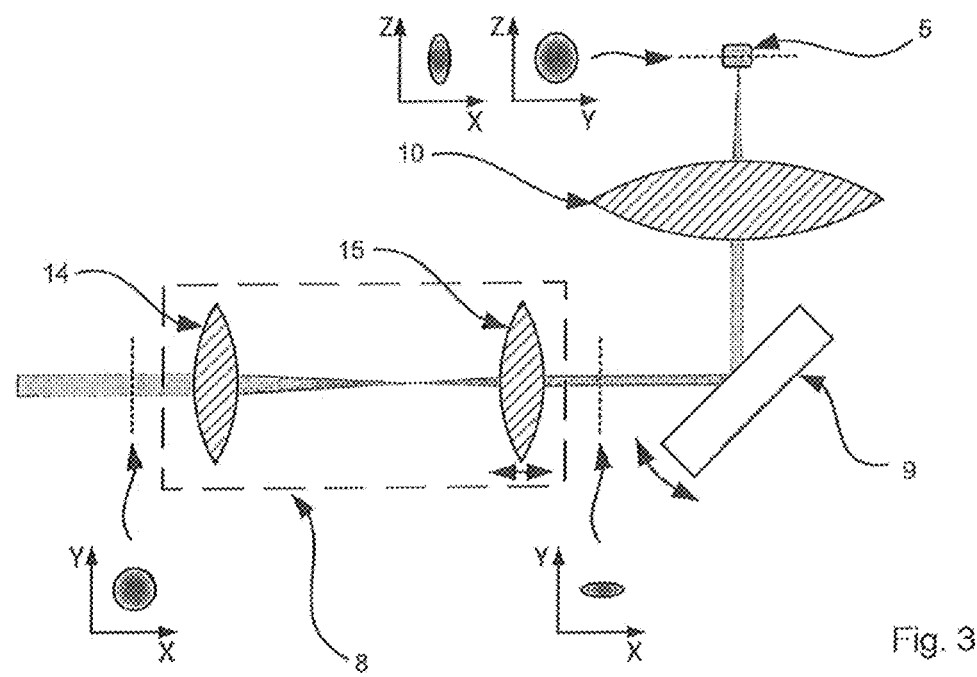
FIG. 3 shows a modified design of the unit for focus volume adjustment.

FIG. 3 shows a modified design of the unit 8 for adapting the focus volume. The unit 8 comprises two coaxial cylindrical lenses 14 and 15 which are spaced apart from one another and through which the beam passes. The beam profile before entering the unit 8, specifically in the plane shown in dashed lines, circular. At the exit from the unit 8, a compression in the direction of the y-axis can be observed. This results in the expansion of the focus point volume shown in the drawing at the focal point 5 in the x-z-plane and in the y-z-plane.

By adjusting the distance between the cylindrical lenses 14 and 15, the volume of the overall focal point 5 changes.

Figure 5:
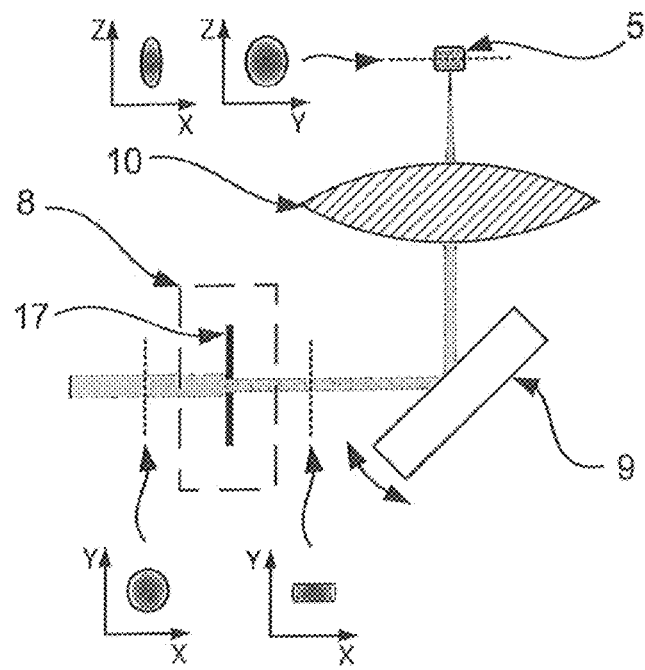
FIG. 5 shows another modified design of the unit for focus volume adjustment.

A similar effect results when a slit diaphragm 17 is used, as shown in the embodiment according to FIG. 5, but here intensity losses arise due to the cutting off of the beam.

Figure 4:
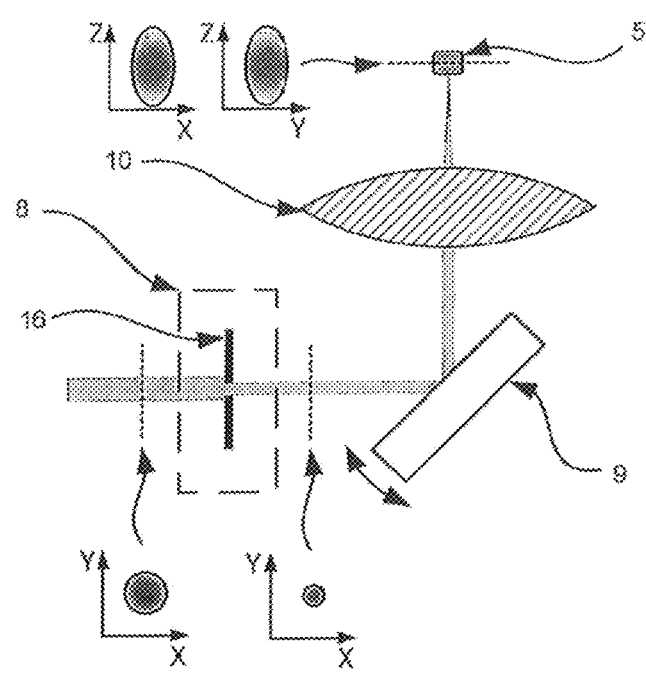
FIG. 4 shows another modified design of the unit for focus volume adjustment.

In the embodiment according to FIG. 4, an iris diaphragm 16 causes a reduction in the effective numerical aperture of the imaging system, as a result of which the focal point volume becomes both longer and wider.

Figure 6:
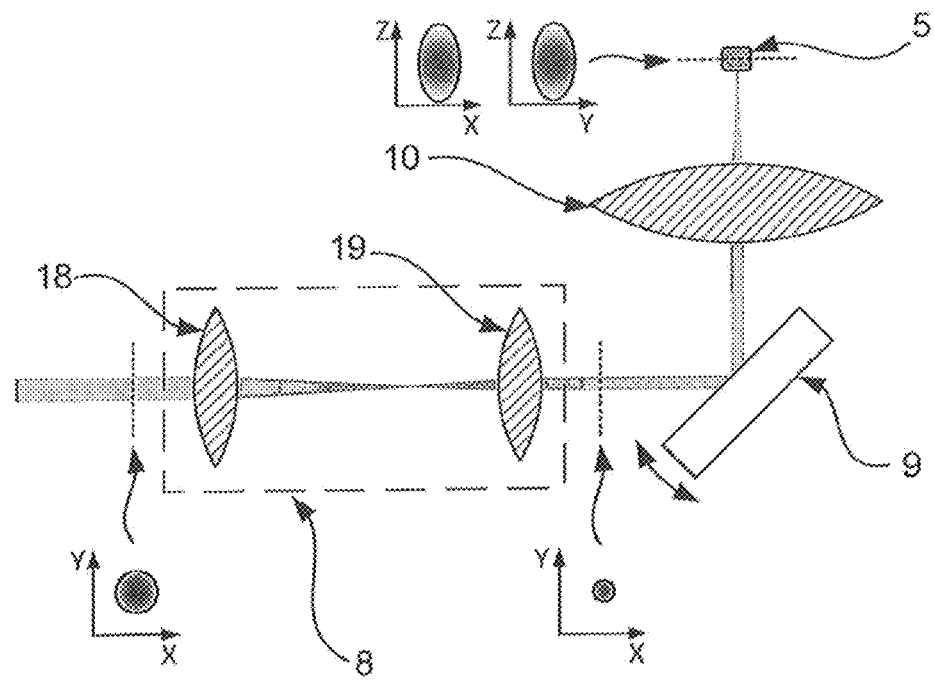
FIG. 6 shows a further modified design of the unit for focus volume adjustment and FIGS. 7a-c show different embodiments of the channel structure in a test body.

The expander shown in the embodiment according to FIG. 6 with the lenses 18 and 19 has the same effect as the iris diaphragm 16, but avoids intensity losses by reducing the beam diameter without cutting off the beam.

The possibilities for changing the focal point volume shown in FIGS. 2 to 6 take place in particular using pulsed laser light with a wavelength in the range from 400 to 1600 nm, the pulse length being between 1 fs and 1 ns.

Figure 7A:
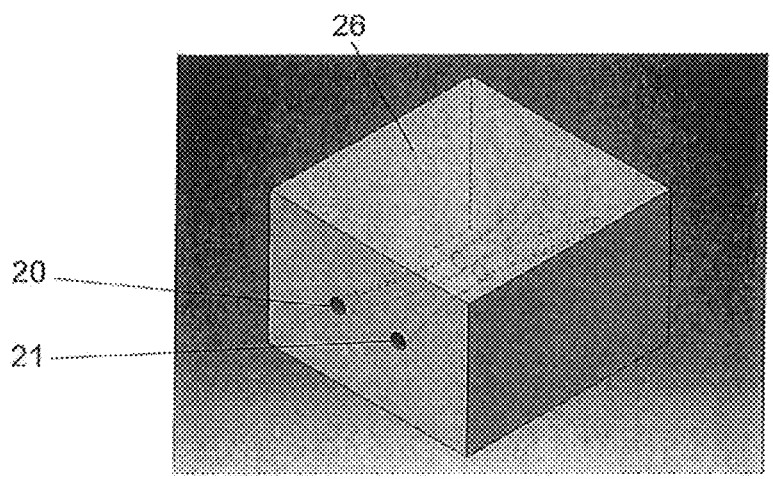
Figure 7B:
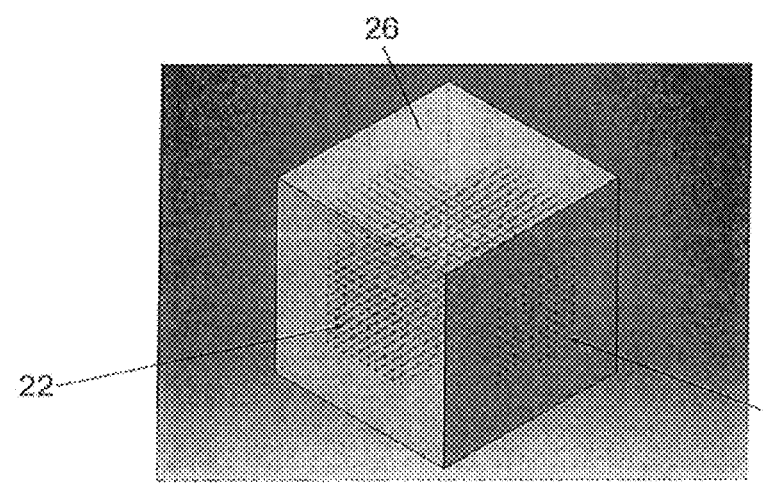
Figure 7C:
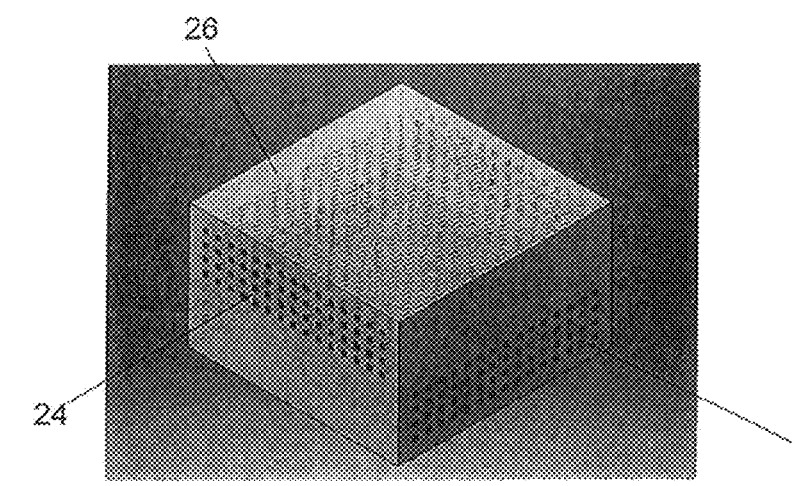

FIGS. 7a-7c now show models of a test body with different channel structures created with suitable software. In FIG. 7a, a pair of channels 20, 21 can be seen as an example, which is designed to be tangent. In FIG. 7b intersecting channel bundles 22, 23 are formed, wherein the channels of the individual bundles 22, 23 are formed interleaving. In the embodiment according to FIG. 7c, however, the channels of the intersecting channel bundles 24, 25 are formed in mutually different sections of the test body 26.

In an experiment, the various test bodies according to FIGS. 7a-c were manufactured with the aid of a multiphoton absorption process or a multiphoton lithography process.

In the case of a cube-shaped test body made of ETA-TTA with an edge length of 2.5 mm and tightly packed 10 µm channels, a slight increase in anisotropy could be measured without a clear preferred direction within the test body. In the next 7.0×7.0×1.5 mm$^3$ test print with a 200×40 channel array with a channel cross section of 20×20 µm, a significant increase in the anisotropy in the direction of the channel was measured. In order to rule out errors in the measurement, a further 6.0×6.0×2.5 mm$^3$ test body with a channel bundle comprising 121×40 channels and a channel bundle running perpendicular thereto comprising 121×40 channels was produced and embedded in gelatine. This arrangement was then measured with the help of a 7 Tesla full-body scanner because it was now large enough. In the structural turbo-spin-echo measurements (TSE measurements) carried out, it was possible to precisely reconstruct the structure of the test bodies including the individual printing areas. The diffusion measurements using diffusion-weighted echo planar imaging recordings (EPI recordings) showed a significant increase in the anisotropy within the test body channels and no anisotropy outside the test body channels. It could also be demonstrated that the anisotropy runs approximately parallel to the channels.

The invention claimed is:

1. A method of producing a test body for diffusion tensor imaging, which comprises a plurality of channels in a structuring material, the channels having a maximum cross-section of 625 µm$^2$, the method comprising:
    creating a virtual model of the test body,
    feeding the virtual model to a structuring device,
    the structuring device producing the test body by means of a 3D printing-based structuring process, the structuring process being designed as a multi photon lithography process wherein the structuring process comprises irradiating the structuring material containing a photosensitizer or photoinitiator in a location-selective manner, wherein radiation is successively focused on focal points lying within the structuring material, resulting in that in each case a volume element of the structuring material located in a focal point is subjected to a change in state by means of a photochemical reaction as a result of multi photon absorption and in that the plurality of channels is created in the structuring material.

2. Method according to claim 1, wherein the structuring process is designed as an additive method in which the volume element of the structuring material located in the respective focal point is solidified.

3. Method according to claim 1, wherein the structuring process is designed as a subtractive method in which the volume element of the structuring material located in the respective focal point is photo-degraded.

4. Method according to claim 1, wherein the volume of the focal point is varied during the method in such a way that the test body comprises state-changed volume elements of a first group and state-changed volume elements of a second group, wherein the volume elements of the first group have a smaller volume than the volume elements of the second group.

5. Method according to claim 1, wherein the volume of the focal point is varied during the method in such a way that the test body comprises solidified volume elements of a first group and solidified volume elements of a second group, wherein the volume elements of the first group have a smaller volume than the volume elements of the second group, and wherein the first group of solidified volume elements form channel walls of said channels and the second group of solidified volume elements form regions lying between the channel walls.

6. Method according to claim 4, wherein the volume of the focal point is varied during the method in such a way that the test body comprises photo-degraded volume elements of a first group and photo-degraded volume elements of a second group, wherein the volume elements of the first group have a smaller volume than the volume elements of the second group, and wherein the first group of photo-degraded volume elements form channel walls of said channels and the second group of photo-degraded volume elements form an interior of the channels.

7. Method according to claim 4, wherein the volume of the focal point is varied during the method such that the state-changed volume elements of the first group have a volume that is less than 50% of the volume of state-changed volume elements of the second group.

8. Method according to claim 1, wherein the test body comprises a first group of channels and a second group of channels, the channels of the first group and the channels of the second group not running parallel to one another.

9. Method according to claim 8, wherein the channels of the first group cross the channels of the second group, preferably at a right angle.

10. Method according to claim 8, wherein the channels of the first and second groups are curved and have a common tangent.

11. Method according to claim 2, wherein at least one acrylate- or methacrylate-based photopolymer, mixed with a photoinitiator, is used as the structuring material.

12. Method according to claim 3, wherein the structuring material contains a photosensitizer and the photosensitizer is designed for the photochemical cleavage of photolabile bonds contained in the structuring material wherein the photosensitizer transfers the absorbed energy to the photolabile bonds as a result of two-photon absorption without experiencing intramolecular cleavage, and thereby causes their cleavage.

13. Method according to claim 12, wherein the structuring material contains the photolabile bonds to be cleaved in a matrix formed by a polymer network.

14. Method according to claim 13, wherein the polymer network is a gel.

15. Method according to claim 14, wherein the gel is allowed to swell with a solution of the photosensitizer in a suitable solvent in order to distribute the photosensitizer within the gel before the irradiation takes place.

16. Method according to claim 12, wherein a solution of the photosensitizer with a concentration of about 0.01 mM to about 1 mM is used.

17. Method according to claim 12, wherein the photosensitizer is selected from the class of benzylidene ketones, including one of the initiators P2CK, G2CK and E2CK shown below:

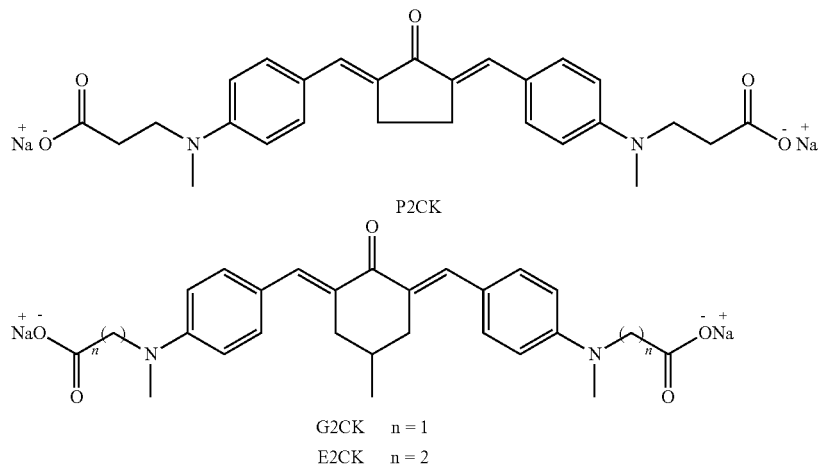

18. Test body for diffusion tensor imaging, produced using a method according to claim 1.

19. Method of calibrating a magnetic resonance tomograph, comprising subjecting a test body according to claim 18 to a diffusion MRT in order to obtain diffusion data and subjecting the diffusion data to a quantitative analysis with regard to diffusion coefficients in different directions, the result of the diffusion coefficient analysis being compared with a reference value in the test body and any deviations are used to calibrate the magnetic resonance tomograph.

20. Method of calibrating a magnetic resonance tomograph, comprising subjecting a test body according to claim 18 to a diffusion MRT in order to obtain diffusion data and subjecting the diffusion data to a tractography, the result of the tractography being compared with a course of the channels in the test body and any deviations being used for the calibration of the magnetic resonance tomograph.

* * * * *